US008568780B2

(12) United States Patent
Kolter et al.

(10) Patent No.: US 8,568,780 B2
(45) Date of Patent: *Oct. 29, 2013

(54) PHARMACEUTICAL FORMULATION FOR THE PRODUCTION OF RAPIDLY DISINTEGRATING TABLETS

(75) Inventors: Karl Kolter, Limburgerhof (DE); Michael Schönherr, Frankenthal (DE); Silke Gebert, Grünstadt (DE); Kathrin Meyer-Böhm, Feucht (DE); Angelika Maschke, Regensburg (DE)

(73) Assignee: BASF SE, Ludwigshafen (DE)

( * ) Notice: Subject to any disclaimer, the term of this patent is extended or adjusted under 35 U.S.C. 154(b) by 319 days.

This patent is subject to a terminal disclaimer.

(21) Appl. No.: 12/663,036

(22) PCT Filed: Jun. 2, 2008

(86) PCT No.: PCT/EP2008/056763
§ 371 (c)(1),
(2), (4) Date: Dec. 4, 2009

(87) PCT Pub. No.: WO2008/148731
PCT Pub. Date: Dec. 11, 2008

(65) Prior Publication Data
US 2010/0173859 A1 Jul. 8, 2010

(30) Foreign Application Priority Data
Jun. 6, 2007 (EP) .................................. 07109717

(51) Int. Cl.
A61K 9/00 (2006.01)
A61K 47/26 (2006.01)
A61K 47/34 (2006.01)
A61K 47/36 (2006.01)
A61K 47/38 (2006.01)
A61K 9/20 (2006.01)

(52) U.S. Cl.
USPC .................... 424/489; 424/465; 514/772.3

(58) Field of Classification Search
CPC .................... A61K 9/0056; A61K 9/1605
See application file for complete search history.

(56) References Cited

U.S. PATENT DOCUMENTS

| | | | |
|---|---|---|---|
| 4,658,002 A | 4/1987 | Tschang et al. | |
| 5,569,469 A | 10/1996 | Lovrecich | |
| 6,066,334 A * | 5/2000 | Kolter et al. | 424/465 |
| 6,274,727 B1 | 8/2001 | Maul et al. | |
| 6,329,334 B1 | 12/2001 | Bertleff et al. | |
| 6,495,177 B1 | 12/2002 | deVries et al. | |
| 6,677,417 B2 | 1/2004 | Meffert et al. | |
| 6,696,085 B2 | 2/2004 | Rault et al. | |
| 6,723,348 B2 | 4/2004 | Faham et al. | |
| 2001/0010825 A1 | 8/2001 | Shimizu et al. | |
| 2001/0016728 A1 | 8/2001 | Kelley | |
| 2002/0071864 A1 | 6/2002 | Kim et al. | |
| 2002/0168404 A1 | 11/2002 | Rault et al. | |
| 2003/0124184 A1 * | 7/2003 | Mezaache et al. | 424/465 |
| 2004/0058896 A1 | 3/2004 | Dietrich et al. | |
| 2004/0110661 A1 | 6/2004 | Dietrich et al. | |
| 2005/0244343 A1 | 11/2005 | Witham et al. | |
| 2005/0244492 A1 | 11/2005 | Mehra et al. | |
| 2006/0251716 A1 * | 11/2006 | Norman et al. | 424/464 |
| 2008/0299191 A1 | 12/2008 | Kolter et al. | |
| 2008/0299194 A1 | 12/2008 | Kolter et al. | |
| 2010/0178306 A1 | 7/2010 | Kolter et al. | |
| 2010/0178349 A1 | 7/2010 | Kolter et al. | |
| 2010/0184785 A1 | 7/2010 | Kolter et al. | |

FOREIGN PATENT DOCUMENTS

| | | |
|---|---|---|
| EP | 0177812 A1 | 4/1986 |
| EP | 0839526 A2 | 5/1998 |
| EP | 1036839 A2 | 9/2000 |
| JP | 2004026521 A | 1/2004 |
| JP | 2004265216 A | 9/2004 |
| WO | WO-98/22094 A2 | 5/1998 |
| WO | WO-03/032978 A1 | 4/2003 |
| WO | WO-03/041683 A2 | 5/2003 |
| WO | WO-03/051338 A1 | 6/2003 |
| WO | WO-03/072084 A1 | 9/2003 |
| WO | WO-2005/105049 A2 | 11/2005 |

(Continued)

OTHER PUBLICATIONS

See BASF, Accelerators—Kollidon CL, Kollidon CL-F, Kollidon CL-SF, Kollidon CL-M at http://www.basf-chemtrade.de/images/stories/broschueren/PHI/basf_kollidon_grades.pdf—accessed Nov. 23, 2009.
Bühler, V. "Polyvinylpyrrolidone Excipients for Pharmaceuticals," Springer Verlag Berlin Heidelberg, pp. 128-131, 2005.

Primary Examiner — Daniel Sullivan
Assistant Examiner — Lisbeth C Robinson
(74) Attorney, Agent, or Firm — Novak Druce Connolly Bove + Quigg LLP

(57) ABSTRACT

Pharmaceutical formulation in the form of compacts comprising
A) an agglomerated excipient content composed of
  a1) 60-97% by weight of sugar or sugar alcohols,
  a2) 1-25% by weight of a disintegrant, selected from the group consisting of crospovidone, croscarmellose, sodium carboxymethylstarch and L-hydroxypropylcellulose,
  a3) 1-15% by weight of water-insoluble, film-forming polymers
  a4) 0-15% by weight of water-soluble polymers and
  a5) 0-15% by weight of further pharmaceutically customary excipients, the total of the components a1) to a5) being 100% by weight,
B) at least one active ingredient,
C) 0 to 10% by weight, based on the total amount of A) to D), of a lubricant or mold release agent, and
D), if appropriate, further pharmaceutical excipients.

23 Claims, No Drawings

(56) References Cited

FOREIGN PATENT DOCUMENTS

| WO | WO-2006/029787 | A1 | 3/2006 |
| WO | WO-2007/071580 | A1 | 6/2007 |
| WO | WO-2007/071581 | A2 | 6/2007 |
| WO | WO-2008/148733 | A2 | 12/2008 |
| WO | WO-2008/148734 | A1 | 12/2008 |
| WO | WO-2008/148742 | A2 | 12/2008 |

* cited by examiner

PHARMACEUTICAL FORMULATION FOR THE PRODUCTION OF RAPIDLY DISINTEGRATING TABLETS

RELATED APPLICATIONS

This application is a national stage application (under 35 U.S.C. §371) of PCT/EP2008/056763, filed Jun. 2, 2008, which claims benefit of European Application No. 07109717.4, filed Jun. 6, 2007.

The present invention relates to pharmaceutical formulations in the form of compacts for the production of rapidly disintegrating tablets, comprising sugar or sugar alcohols, disintegrant and water-insoluble polymers.

Tablets which disintegrate rapidly in the mouth and/or dissolve rapidly are becoming increasingly important for the oral administration of medicinal substances. Such tablets must disintegrate within a short time, preferably within 30 seconds, in the oral cavity and have a pleasant taste and must not leave behind a gritty sensation. Furthermore they should be easy to produce, with direct tableting having considerable advantages over wet granulation, and should have high mechanical strength so that they withstand packaging procedures, transport and also pressing out from packaging without damage.

The products and processes described to date do not meet these requirements or do so only very inadequately.

Rapidly disintegrating tablets frequently consist of sugar and sugar alcohols, effervescent systems, microcrystalline cellulose and other water-insoluble fillers, calcium hydrogen phosphate, cellulose derivatives, cornstarch or polypeptides. Furthermore, water-soluble polymers, conventional disintegrants (crosslinked PVP, sodium and calcium salts of crosslinked carboxymethylcellulose, the sodium salt of carboxymethyl starch, low-substituted hydroxypropylcellulose L-HPC) and substantially inorganic water-insoluble constituents (silicas, silicates, inorganic pigments) are used. Furthermore, the tablets may also comprise surfactants.

WO 2003/051338 describes a directly tablettable and readily compressible excipient formulation which comprises mannitol and sorbitol. First, an excipient premix is prepared by dissolution of mannitol and sorbitol in water and subsequent spray drying (customary spray drying and SBD method). Mannitol may also be added to this coprocessed mixture. Tablets which additionally comprise disintegrant, glidant, pigment and an active ingredient are said to disintegrate within 60 seconds in the oral cavity.

U.S. 2002/0071864 A1 describes a tablet which disintegrates within 60 seconds in the oral cavity and is mainly formulated from a physical mixture of spray-dried mannitol and a coarse-particle crosslinked polyvinylpyrrolidone and a limited selection of active ingredients. These tablets have a hardness of about 40 N and produce an unpleasant, gritty mouthfeel.

According to U.S. Pat. No. 6,696,085 B2 a methacrylic acid copolymer of type C is to be used as a disintegrant. The methacrylic acid copolymer of type C is a polymer which is resistant to gastric fluid and insoluble in the acidic pH range but water-soluble in the pH range of 7 as is present in the oral cavity. In addition to low hardness (<20 N), the tablets have high friability (>7%) and have a high proportion in the region of 15% by weight of a coarse-particle disintegrant. They consequently have low mechanical strength and, owing to the high proportion of coarse-particle disintegrant, produce an unpleasant, gritty mouthfeel.

EP 0839526 A2 describes a pharmaceutical dosage form consisting of an active ingredient, erythritol, crystalline cellulose and a disintegrant. Furthermore, mannitol is incorporated and crosslinked polyvinylpyrrolidone is used as a disintegrant, so that a physical mixture forms. The tablets are said to decompose within 60 seconds in the oral cavity.

The application JP 2004-265216 describes a tablet which disintegrates in the mouth within 60 seconds and consists of an active ingredient, a water-soluble polyvinyl alcohol/polyethylene glycol copolymer, sugar/sugar alcohol (mannitol) and disintegrant.

It was an object of the present invention to provide tablets which disintegrate rapidly in the mouth, leave behind a pleasant mouthfeel, are mechanically very stable and exhibit good content uniformity, and processes for the production thereof.

Accordingly, a pharmaceutical preparation for the production of tablets which disintegrate rapidly in the mouth was found, which tablets consist of compacts obtainable from A) an agglomerated excipient content composed of
  a1) 60-97% by weight of at least one sugar or sugar alcohol or mixtures thereof,
  a2) 1-25% by weight of a disintegrant, selected from the group consisting of crosslinked polyvinylpyrrolidone, croscarmellose, crosslinked sodium carboxymethyl-starch and L-hydroxypropylcellulose,
  a3) 1-15% by weight of water-insoluble polymers,
  a4) 0-15% by weight of water-soluble polymers, and
  a5) 0-15% by weight of further pharmaceutically customary excipients, the total of the components a1) to a5) being 100% by weight,
B) at least one active pharmaceutical ingredient,
C) 0 to 10% by weight, based on the total amount of A) to D), of a lubricant or mold release agent,
D), if appropriate, further pharmaceutical excipients.

Furthermore, a process for the production of such compacts was found, which is distinguished in that the agglomerated excipient content A) is processed in a compactor with B) at least one active ingredient, C) lubricant and D), if appropriate, further excipients.

Furthermore, tablets which disintegrate rapidly in the mouth and are obtainable from such compacts were found. The tablets disintegrate in the mouth or in an aqueous medium within 60 seconds, preferably within 30 seconds, particularly preferably within 20 seconds. "The tablets exhibit a disintegration time of <60 seconds in phosphate buffer, pH 7.2, at 37° C. The disintegration time is determined in a disintegration tester complying with USP or Pharm. Fur."

The pharmaceutical preparations comprise, as component a1), from 60 to 97% by weight, preferably from 70 to 95% by weight, particularly preferably from 75 to 93% by weight, of a sugar, sugar alcohol or mixtures thereof. Suitable sugars or sugar alcohols are trehalose, mannitol, erythritol, isomalt, maltitol, lactitol, xylitol and sorbitol. The sugar or sugar alcohol components are preferably finely divided, with average particle sizes of from 5 to 100 μm. If desired, the particle sizes can be adjusted by grinding. Preferred particle sizes are from 30 to 50 μm. However, it may also be advisable to use particle sizes smaller than 30 μm. It may likewise be advisable to employ sugars or sugar alcohols which comprise mixtures of fractions differing in particle size, for example mixtures of 30 to 70% by weight of a particle size fraction having an average particle size of <30 μm and 30 to 70% by weight of a particle size fraction having an average particle size of 30 to 50 μm. Mannitol, erythritol or mixtures thereof are preferably employed.

Disintegrants in amounts of from 1 to 25% by weight, preferably 2 to 15% by weight, particularly preferably 3 to 10% by weight, are employed as component a2). Such disintegrants are water-insoluble but non film-forming. Suitable disintegrants are crosslinked polyvinylpyrrolidone, croscarmellose, a crosslinked carboxymethylcellulose, croscarmellose also being understood according to the invention to mean the sodium and calcium salts thereof. Furthermore, sodium carboxymethylstarch is suitable. Likewise suitable is L-hydroxypropylcellulose, preferably having 5 to 16% hydroxypropoxy groups, as described in USP/NF 2005.

Water-insoluble polymers in amounts of from 1 to 15% by weight, preferably from 1 to 15% by weight, are used as component a3). These are polymers. Preferred polymers are those which are insoluble in the pH range from 1 to 14, i.e. have a water insolubility which is pH independent at every pH. However, polymers which are water-insoluble at any pH in the pH range from 6 to 14 are also suitable.

The polymers should be film-forming polymers. In this context, film-forming means that the polymers have a minimum film forming temperature of from −20 to +150° C., preferably from 0 to 100° C., in aqueous dispersion.

Suitable polymers are polyvinyl acetate, ethylcellulose, methyl methacrylate/ethyl acrylate copolymers, ethyl acrylate/methyl methacrylate/trimethylammoniumethyl methacrylate terpolymers. Butyl methacrylate/methyl methacrylate/dimethylaminoethyl methacrylate terpolymers.

The acrylate/methacrylate copolymers are described in more detail in the European Pharmacopoeia as Polyacrylate Dispersion 30%, in the USP as Ammonio Methacrylate Copolymer and in JPE as Aminoalkyl Methacrylate Copolymer E.

Polyvinyl acetate is used as preferred component c). This may be used as an aqueous dispersion having solids contents of from 10 to 45% by weight. In addition, a preferred polyvinyl acetate is one having a molecular weight of from 100 000 to 1 000 000 daltons, particularly preferably from 200 000 to 800 000 daltons.

Furthermore, the formulations may comprise water-soluble polymers in amounts of from 0 to 15% by weight as component a4). Suitable water-soluble polymers are, for example, polyvinylpyrrolidones, vinylpyrrolidone/vinyl acetate copolymers, polyvinyl alcohols, polyvinyl alcohol/polyethylene glycol graft copolymers, polyethylene glycols, ethylene glycol/propylene glycol block copolymers, hydroxypropylmethylcellulose, hydroxypropylcellulose, hydroxyethylcellulose, carrageenans, pectins, xanthans and alginates.

If desired, taste and appearance of the tablets obtained from the formulations can be further improved by adding pharmaceutically customary excipients (components a5)) in amounts of from 0 to 15% by weight, for example such as acidifiers, buffer substances, sweeteners, flavors, flavor enhancers and colorants. The following substances are particularly suitable here: citric acid, tartaric acid, ascorbic acid, sodium dihydrogen phosphate, cyclamate, saccharin sodium, aspartame, menthol, peppermint flavor, fruit flavors, vanilla flavor, glutamate, riboflavin, beta-carotene, water-soluble colorants and finely divided color lakes.

By adding thickeners, such as high molecular weight polysaccharides, the mouthfeel can be additionally improved by increasing the softness and the sensation of volume. Furthermore, surfactants may also be added as components a5). Suitable surfactants are, for example, sodium lauryl sulfate, dioctyl sulfosuccinate, alkoxylated sorbitan esters, such as polysorbate 80, polyalkoxylated derivatives of castor oil or hydrogenated castor oil, for example Cremophor® RH 40, alkoxylated fatty acids, alkoxylated hydroxyl fatty acids, alkoxylated fatty alcohols, alkali metal salts of fatty acids and lecithins.

Furthermore, finely divided pigments may also be added for further improvement of the disintegration, because they increase the internal interfaces and hence water can penetrate more rapidly into the tablet. These pigments, such as iron oxides, titanium dioxide, colloidal or precipitated silica, calcium carbonates or calcium phosphates, must of course be very finely divided since otherwise a grainy taste once again results.

The agglomerates A) used according to the invention are in principle suitable for processing with all active ingredients B). The granules are especially suitable for the production of pharmaceutical forms having the dosage of the respective active ingredient stated below, it also being possible to use the active ingredient in taste-masked form:

Zolmitriptan 2.5 mg, rizatriptan 5 mg, diphenhydramine HCl (taste-masked) 20 mg, brompheniramine 5 mg, chlorpheniramine 5 mg, pseudoephedrine (taste-masked) 30 mg, paracetamol (taste-masked) 250 mg, ibuprofen (taste-masked) 200 mg, acetylsalicylic acid 250 mg (taste-masked), hyoscyamine sulfate 0.125 mg, mirtazapine 15 mg, selegeline HCl 1.25 mg, ondansetron 4 mg, olanzapine 5 mg, clonazepam 1 mg, cetirizine hydrochloride 10 mg, desloratadine 5 mg, enalapril maleate 5 mg, domperidone maleate 10 mg, scopolamine 0.25 mg, oxazepam 15 mg, lorazepam 2.5 mg, clozapine 25 mg, dihydroergotamine mesylate 5 mg, nicergoline 5 mg, phloroglucinol 80 mg, metopimazine 7.5 mg, triazolam 0.5 mg, protizolam 0.5 mg, tramadol 50 mg, zolpidem tartrate 5 mg, cisapride, risperidone 2 mg, azithromycin 100 mg (taste-masked), roxithromycin 50 mg (taste-masked), clarithromycin 125 mg (taste-masked), erythromycin estolate 250 mg (taste-masked), apomorphine 20 mg, fentanyl 0.6 mg.

The compacts may further comprise as component C) a lubricant in amounts of from 0 to 10% by weight, preferably 0.2 to 5% by weight. Suitable lubricants are magnesium stearate, calcium stearate, aluminum stearate, stearic acid, stearyl alcohol, cetyl alcohol, glyceryl monostearate, glyceryl monobehenate, glyceryl palmitostearate, palmitic acid, myristic acid, behenic acid, capric acid, myristyl alcohol, polyethylene glycol, poloxamers, talc or sodium benzoate. Further lubricants which can be used are indicated in the book "Die Tablette", W. Ritschel and A. Bauer-Brandl, 2nd edition, 2002, Editio Cantor Verlag Aulendorf.

It is furthermore possible to add as components D also further pharmaceutical excipients in amounts of from 0% by weight to 30% by weight, preferably 0 to 15% by weight, to the mixture for compaction. Suitable as component D are the substances mentioned under a1) to a5), as well as fillers such as microcrystalline cellulose, starch or degraded or modified starch. it is thus also possible to incorporate colorants, sweeteners, flavorings, further disintegrants, carbonates, bicarbonates, acidifiers or further excipients. The use of colorants, in which case it is possible to use inorganic pigments, organic color lakes or water-soluble colorants, leads for example to uniformly colored, rapidly disintegrating tablets. Examples of suitable colorants are riboflavin, beta-carotene, anthocyans, carmine, indigocarmine, orange yellow S, quinoline yellow, indigotine lake, brilliant blue, sunset yellow. These further substances can be added in solid form. According to a preferred embodiment of the invention, further disintegrants may be added as component D).

The formulations used according to the invention can be produced by agglomeration in mixers, fluidized-bed apparatuses or spray towers. Solid starting materials and granulating liquid are first mixed with one another and the moist mixed material is then dried. According to the present invention, the granulating liquid used is an aqueous dispersion of component c), of the water-insoluble polymer.

In fluidized-bed agglomeration, an aqueous dispersion of the water-insoluble polymer is sprayed onto a fluidized mixture of sugar or sugar alcohol and crosslinked PVP, resulting in the agglomeration of the fine particles. The inlet air temperatures are 30 to 100° C., and the outlet air temperatures are 20 to 70° C.

In production in spray towers, the so-called FSD or SBD technology (FSD: fluidized spray drying; SBD: spray bed drying) is preferably used. Here, a solution of the sugar or sugar alcohol in water is first spray-dried and the addition of crosslinked PVP and the spraying in of an aqueous dispersion of the water-insoluble polymer are effected in the lower part of the spray dryer or in a connected fluidized bed, with the result that the particles agglomerate. Fine particles can furthermore be blown again in front of the spray nozzle of the sugar or sugar alcohol solution and additionally agglomerated. A procedure starting from the crystalline form of the sugar or sugar alcohol is also possible in the spray tower, FSD or SBD. The crystalline sugar or sugar alcohol is added at the top of the spray tower or in the recycle stream of fine material. By spraying an aqueous dispersion of the water-insoluble polymer, this crystalline solid is agglomerated in the tower.

It may prove advantageous for the agglomeration process to carry out a multistage spray process. At the beginning, the spray rate is kept low in order to prevent over-moistening of the initially charged product and hence adhesion thereof. With increasing duration of the process, the spray rate can be increased and thus the tendency to agglomerate can be raised. It is also possible to adapt the inlet air flow rate and/or temperature in an appropriate manner during the process. Particularly during the drying phase, it is advantageous to reduce the inlet air flow rate and hence to prevent abrasion of the agglomerates due to a high mechanical stress.

The fineness of the spray droplet of the binder solution or dispersion (adjustable via the atomization gas pressure), the nozzle geometry and the distance from the nozzle to the atomization gas pressure), the nozzle geometry and the distance from the nozzle to the product bed may be regarded as further adaptation parameters for the agglomerate size. The finer and more uniform the spraying, the finer and more uniform are the resulting agglomerates. The further away the nozzle is from the product bed, the poorer is the agglomeration behavior.

Furthermore, the agglomerates can also take place in a mixer by continuous aggregation with mixing. Such a continuous form of aggregation with mixing is the so-called "Schugi granulation". There, solid starting materials and the granulating liquid comprising the water-insoluble polymer are thoroughly mixed with one another in a continuously operating vertically arranged high-speed mixer (cf. also M. Bohnet, "Mechanische Verfahrenstechnik", Wiley VCH Verlag, Weinheim 2004, page 198 et seq.).

According to a particular embodiment, the disintegrant is suspended in the aqueous dispersion of the water-insoluble polymer.

The agglomerates thus obtained have an average particle size of 100-600 µm, preferably 120-500 µm and particularly preferably 140-400 µm.

The water-insoluble, film-forming polymer serves as an agglomerating agent for agglomerating the fine sugar or sugar alcohol crystals and the particles of disintegrant.

The agglomerates are then processed to compacts.

The principle of compaction is described in the book "Die Tablette", W. Ritschel and A. Bauer-Brandl, 2nd edition, 2002, Editio Cantor Verlag Aulendorf in the Trockene Granulation chapter. So-called roll compactors are preferably employed, where the starting material is compacted between 2 rotating rolls and then comminuted again to produce coarser granule particles. The comminution in this case should take place as gently as possible so that few fines are produced. The compressive forces to be applied are between 0.5 and 20 kN/cm, preferably between 1 and 10 kN/cm. It has proved advantageous to apply compressive forces which are as low as possible and just result in a stable compact, because the hardness of the tablets produced therefrom is then greatest. The comminution is preferably effected by a screening granulator with mesh widths of from 0.5 to 3 mm.

The resulting compacts ordinarily have an average particle size of between 0.2 and 2 mm, preferably between 0.3 and 1 mm.

The compacts can be processed to tablets in a conventional way. For this purpose it is ordinarily worthwhile to admix further lubricant. In a particular embodiment, additional disintegrant is also mixed in at this stage. The tableting takes place on conventional rotary presses, it being possible to produce both biplanar or biconvex forms as well as oblong or football-shaped forms.

The compacts according to the invention can advantageously also be used for the production of tablets which are left to disintegrate in a glass of water prior to use. The production of tablets which are swallowed intact is of course also possible.

It has surprisingly been found that very small standard deviations in tablet mass and active ingredient content are achieved, while at the same time the disintegration of the tablet is rapid, through the compaction. Normally, the compaction brings about a prolongation of the disintegration time through reducing the porosity. Water is then no longer able to penetrate so easily into the cavities in the tablet. This effect of prolongation of disintegration time is not found, or is found to only a small extent, with the formulations of the invention.

The process of the invention is particularly suitable for low-dose medicinal substances because problems with content uniformity occur frequently in these cases. The particular plasticity of components a3) and, in this connection, especially of polyvinyl acetate results in the active ingredient crystals being intimately bonded to the agglomerates of component A, so that segregation is no longer possible. The plasticity additionally ensures that this takes place even with low compacting force, whereby the porosity is substantially retained.

Therefore, the compacts according to the invention have extremely good tableting properties and compressibilities, which lead to mechanically very stable tablets. The hardness of the tablets produced with the aid of the pharmaceutical formulations according to the invention is >40 N. Frequently, the hardnesses are above 60 N, even with the use of active ingredients which are difficult to compress. The friabilities are <0.5%. There is therefore no damage during customary tablet handling.

EXAMPLES

Agglomerates were firstly produced in a fluidized bed (GPCG 3.1, Glatt) by means of a top spray process: sugar alcohol and disintegrant were initially charged and agglomerated with aqueous binder dispersion. A commercially obtainable polyvinyl acetate dispersion (Kollicoat® SR30 D, BASF AG) was used as aqueous binder dispersion.

Batch size: 1.8 kg
Concentration of the binder dispersion: 10% by weight of solid The rapidly disintegrating excipient prepared by fluidized-bed agglomeration was admixed with active ingredient and lubricant (Mg stearate), in the case of formulations C to E with further excipients and then processed further on a compactor (Gerteis Minipactor).

TABLE 1

Compacting process parameters

|  | A – C | D + E |
|---|---|---|
| Batch size [g] | 1400 | 1400 |
| Compressive force [kN/cm] | 6.0 | 4.5 |
| Gap [mm] | 1.0 | 1.5 |
| Screen size [mm] | 1.25 | 1.25 |

TABLE 2

Composition of compacts A to C in % by weight

|  | A | B | C | D | E |
|---|---|---|---|---|---|
| Mannitol ($d_{0.5}$: 36 µm) | 89.1 | 81.61 | 86.4 | 75.5 | 70.3 |
| Kollidon CL-SF*) | 4.95 | 4.53 | 4.8 | 5.5 | 5.0 |
| Kollicoat SR 30 D (solid) | 4.95 | 4.53 | 4.8 | 3.0 | 4.2 |
| Kollidon CL-SF*) | — | — | 1.0 |  |  |
| Croscarmellose sodium |  |  |  |  | 1.5 |
| L-HPC |  |  |  | 2.0 |  |
| Microcrystalline cellulose (Avicel PH 105) |  |  |  |  | 5.0 |
| Sicovit Rot 30 (iron oxide) |  |  |  | 1.5 |  |
| Riboflavin |  |  |  |  | 2.0 |
| Kollidon VA 64 Fine (Copovidon) |  |  |  |  | 1.5 |
| Aspartame |  |  |  | 0.5 | 0.5 |
| Peppermint flavor |  |  |  | 1.0 | 1.0 |
| Loperamid HCl | — | — | 2.0 |  |  |
| Caffeine (fine powder) | — | 8.33 | — | 10.0 | 8.0 |
| Magnesium stearate | 1.0 | 1.00 | 1.0 | 1.0 |  |

*)Crospovidone, average particle size 17 µm

The compacts produced in this way were mixed with 0% to 2% by weight lubricant (Mg stearate) and then compressed in an eccentric tablet press (Korsch XP1) to tablets with a hardness of 40-70N.

The tablets were investigated for hardness (HT-TMB-Cl-12 F tablet tester from Kraemer), disintegration time in phosphate buffer of pH 7.2 (ZT 74 disintegration tester, Erweka) and release rate in gastric fluid (release apparatus, Erweka).

TABLE 3

Tablet properties of formulations A to E

|  | Hardness [N] | Friability [%] | Disintegration time [s] | Release rate [% after 10 min] |
|---|---|---|---|---|
| A | 57 | <0.2 | 57 | — |
| B | 50 | <0.2 | 35 | 100 |
| C | 70 | <0.2 | 51 | 75 |
| D | 53 | <0.2 | 39 | 98 |
| E | 54 | <0.2 | 33 | 97 |

The invention claimed is:

1. A pharmaceutical formulation in the form of compacts comprising
A) an agglomerated excipient content composed of
   a1) 60-97% by weight of sugar or sugar alcohols,
   a2) 1-25% by weight of a disintegrant, selected from the group consisting of crospovidone, croscarmellose, sodium carboxymethylstarch and L-hydroxypropylcellulose,
   a3) 1-15% by weight of polyvinyl acetate
   a4) 0-15% by weight of water-soluble polymers and
   a5) 0-15% by weight of further pharmaceutically customary excipients the total of the components a1) to a5) being 100% by weight,
B) at least one active ingredient;
C) 0 to 10% by weight, based on the total amount of A) to D), of a lubricant or mold release agent, and
D) if appropriate, further pharmaceutical excipients.

2. The formulation according to claim 1 comprising component C in amounts of from 0.2 to 5% by weight.

3. The formulation according to claim 1, comprising a disintegrant as component D.

4. The formulation according to claim 1 comprising magnesium stearate or stearic acid as lubricant.

5. The formulation according to claim 1, comprising mannitol or erythritol or mixtures thereof as sugar alcohol.

6. The formulation according to claim 1, comprising croscarmellose as sodium or calcium salt.

7. The formulation according to claim 1, comprising an L-hydroxypropylcellulose having 5 to 16% hydroxypropoxy groups.

8. The formulation according to claim 1, comprising crospovidone as disintegrant.

9. The formulation according to claim 1, where the polyvinyl acetate is employed in the form of an aqueous dispersion.

10. The formulation according to claim 1, where polyvinylpyrrolidone is used as water-soluble polymer.

11. The formulation according to claim 1, where acidifiers, sweeteners, flavors, flavor enhancers, colorants, thickeners, surfactants and finely divided pigments are used as further pharmaceutically customary excipients.

12. The formulation according to claim 1, comprising agglomerates A) composed of
   a1) 70-95% by weight of sugar or sugar alcohols
   a2) 2-15% by weight of a disintegrant,
   a3) 1-10% by weight of polyvinyl acetate
   a4) 0-2% by weight of water-soluble polyvinylpyrrolidone, and
   a5) 0-15% by weight of further pharmaceutically customary excipients.

13. The formulation according to claim 1, comprising agglomerates A) composed of
   a1) 75-95% by weight of mannitol or erythritol or a mixture thereof,
   a2) 3-10% by weight of a disintegrant,
   a3) 1-10% by weight of polyvinyl acetate,
   a4) 0-2% by weight of water-soluble polyvinylpyrrolidone, and
   a5) 0-15% by weight of further pharmaceutically customary excipients.

14. The formulation according to claim 1, obtainable by agglomerating the individual components a1) to a5) in a first process step and subjecting the agglomerates A) thus obtained to a compaction together with components B), C) and D).

15. A tablet obtained using a pharmaceutical formulation according to claim 1, where the tablet has a disintegration time of less than 40 seconds.

16. The tablet according to claim 15, where the tablet has a hardness greater than 40 N.

17. The tablet according to claim 15 or 16, comprising from 20 to 99% by weight, based on the total tablet weight, of said pharmaceutical formulation.

18. The tablet according to claim 15, comprising further excipients.

19. A process for producing a pharmaceutical formulation in the form of compacts according to claim 1, which comprises initially agglomerating
   A) an excipient content composed of
   a1) 60-97% by weight of sugar or sugar alcohols,
   a2) 1-25% by weight of a disintegrant
   a3) 1-15% by weight of polyvinyl acetate,
   a4) 0 to 2% by weight of water-soluble polyvinylpyrrolidone, and a5) 0-15% by weight of further pharmaceutically customary excipients the total of the components a1) to a5) being 100% by weight, in the presence of water,
   and then feeding the agglomerates thus obtained to a compaction together with B) at least one active ingredient, C), if appropriate, a disintegrant, and D), if appropriate, further pharmaceutical excipients.

20. The tablet of claim 17, wherein said pharmaceutical formulation comprises agglomerates A) composed of
   a1) 75-95% by weight of mannitol or erythritol or a mixture thereof,
   a2) 3-10% by weight of a disintegrant,
   a3) 1-10% by weight of polyvinyl acetate,
   a4) 0-2% by weight of water-soluble polyvinylpyrrolidone, and
   a5) 0-15% by weight of further pharmaceutically customary excipients.

21. The tablet of claim 17, wherein said pharmaceutical formulation is obtainable by agglomerating the individual components a1) to a5) in a first process step and subjecting the agglomerates A) thus obtained to a compaction together with components B), C) and D).

22. The process according to claim 19, wherein the compacting takes place by roll compaction.

23. The tablet of claim 17, wherein said pharmaceutical formulation comprises crospovidone as disintegrant.

* * * * *